United States Patent
Meijer

(10) Patent No.: US 9,486,544 B2
(45) Date of Patent: Nov. 8, 2016

(54) MANGANESE CHELATES AND THEIR USE AS CONTRAST AGENTS IN MAGNETIC RESONANCE IMAGING (MRI)

(75) Inventor: Andreas Meijer, Oslo (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 13/510,064

(22) PCT Filed: Dec. 17, 2010

(86) PCT No.: PCT/EP2010/070029
§ 371 (c)(1),
(2), (4) Date: May 16, 2012

(87) PCT Pub. No.: WO2011/073371
PCT Pub. Date: Jun. 23, 2011

(65) Prior Publication Data
US 2012/0244081 A1    Sep. 27, 2012

(30) Foreign Application Priority Data

Dec. 18, 2009 (NO) .................................. 20093555

(51) Int. Cl.
*A61B 5/055* (2006.01)
*A61K 49/10* (2006.01)
*C07D 471/04* (2006.01)

(52) U.S. Cl.
CPC ........... *A61K 49/106* (2013.01); *C07D 471/04* (2013.01); *A61K 49/10* (2013.01)

(58) Field of Classification Search
CPC combination set(s) only.
See application file for complete search history.

(56) References Cited

U.S. PATENT DOCUMENTS

| 5,334,371 A | 8/1994 | Gries et al. |
| 5,428,139 A * | 6/1995 | Kiefer et al. ................... 534/10 |
| 2008/0305049 A1 | 12/2008 | Degani |

FOREIGN PATENT DOCUMENTS

| WO | 94/26313 | 11/1994 |
| WO | 2006/080022 | 8/2006 |

OTHER PUBLICATIONS

Aime, et.al. Journal of Medicinal Chemistry, vol. 43, No. 21, Oct. 19, 2000 pp. 4017-4024.
PCT/EP2010/070029 ISRWO Dated Apr. 12, 2011.

* cited by examiner

*Primary Examiner* — Michael G Hartley
*Assistant Examiner* — Melissa Perreira
(74) *Attorney, Agent, or Firm* — Wood IP LLC

(57) ABSTRACT

The present invention relates to manganese(II). The invention also relates to manganese(II) chelates attached to other molecules and their use as contrast agents in magnetic resonance imaging (MRI).

19 Claims, No Drawings

MANGANESE CHELATES AND THEIR USE AS CONTRAST AGENTS IN MAGNETIC RESONANCE IMAGING (MRI)

This application is a filing under 35 U.S.C. 371 of international application number PCT/EP2010/070029, filed Dec. 17, 2010, which claims priority to Norway application number 20093555 filed Dec. 18, 2009, the entire disclosure of which is hereby incorporated by reference.

The invention relates to manganese(II) chelates, said manganese(II) chelates attached to other molecules and their use as contrast agents in magnetic resonance imaging (MRI).

MRI is a medical imaging technique in which areas of the body are visualised via the nuclei of selected atoms, especially hydrogen nuclei. The MRI signal depends upon the environment surrounding the visualised nuclei and their longitudinal and transverse relaxation times, T1 and T2. Thus, in the case when the visualised nucleus is a proton, the MRI signal intensity will depend upon factors such as proton density and the chemical environment of the protons. Contrast agents are often used in MRI in order to improve the imaging contrast. They work by effecting the T1, T2 and/or T2* relaxation time and thereby influence the contrast in the images.

The T1, T2 and/or T2* relaxation times can be optmized for a chelated paramagnetic contrast agent by structural modification. Of particular importance is the presence and residence time of a water molecule bound to the paramagnetic ion and the rotational correlation time of the contrast agent. The presence and residence time of a water molecule, bound to the paramagnetic ion, can be modulated by the choice of paramagnetic ion and the chelating moiety. The rotational correlation time can be modulated by varying the size of the contrast agent.

The paramagnetic ion can interfere with biological pathways and induce toxicity, it is therefore necessary to retain the paramagnetic ion within a chelate. The stability of a paramagnetic complex can be modulated by structural design of the cheland moeity. Of particular interest is the kinetic stability, measured as a dissociation half life, which indicate the degree of inertia towards altered chemical surroundings (i.e. endogenous ions).

Several types of contrast agents have been used in MRI. Blood pool MR contrast agents, for instance superparamagnetic iron oxide particles, are retained within the vasculature for a prolonged time. They have proven to be extremely useful to enhance contrast in the liver but also to detect capillary permeability abnormalities, e.g. "leaky" capillary walls in tumours which are a result of tumour angiogenesis.

Water-soluble paramagnetic chelates, i.e. complexes of a chelator and a paramagnetic metal ion—for instance gadolinium chelates like Omniscan™ (GE Healthcare)—are widely used MR contrast agents. Because of their low molecular weight they rapidly distribute into the extracellular space (i.e. the blood and the interstitium) when administered into the vasculature. They are also cleared relatively rapidly from the body.

The solubility of the paramagnetic chelate in water is also an important factor when they are used as contrast agents for MRI because they are administered to patients in relatively large doses. A highly water-soluble paramagnetic chelate requires a lower injection volume, is thus easier to administer to a patient and causes less discomfort.

Prior art documents reading on paramagnetic chelates often tend to refer to paramagnetic ions in general, but are usually concerned with and designed for gadolinium. As the structural design of a chelate is specific for each paramagnetic ion, a chelate designed for gadolinium will not be optimal, in terms of relaxivity or stability, for other paramagnetic ions such as manganese(II) or iron(III). Gadolinium(III) is the most widely used paramagnetic metal ion for MRI chelates.

WO2006/080022 (Degani et. al.) discloses bifunctional conjugates comprising a receptor ligand moiety associated with malignant tumours and a metal binding moiety and complexes thereof with paramagnetic lanthanide or transition-metals.

U.S. Pat. No. 5,334,371 (Gries et. al.) discloses macrocyclic polyaza bicyclo compounds containing manganese (II) ions. The disclosed manganese(II) compounds are inferior, to the compounds in the current invention, in terms of stability and signal generation cababilities and thus less suited as imaging agents.

The manganese(II) ion is a paramagnetic species with a high spin number and a long electronic relaxation time and the potential of a manganese(II) based high relaxivity contrast agent has been reported in the literature. However, the low stability of manganese chelates has proved to be a problem and has therefore limited the feasibility of the use of such in contrast media.

It is an object of the present invention to provide manganese(II) based chelates that are kinetically stable and show optimal water exchange kinetics, and can be used as MR contrast agents.

Therefore, in a first aspect of the present invention there is provided a compound of formula (I):

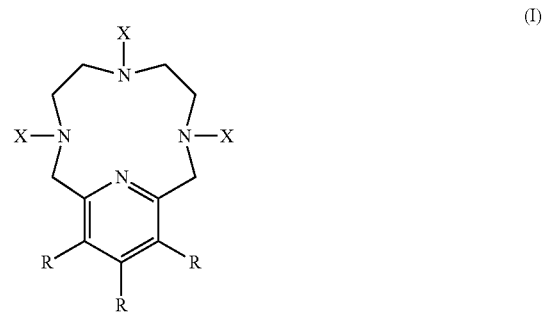

wherein
X is alkyl, $C(Y)_2COOZ$ or a linker;
is alkyl, —PEG, —COOH, —PO(OH)$_2$, —H or a linker;
R is alkyl, —PEG, —N(alkyl)$_2$, —N(PEG)$_2$, —O(alkyl), —O(PEG), —NMe$_2$, —NH$_2$, —OMe, —OH, —H or a linker; and
Z is Mn(II) or —H;
with the proviso that two of the three X groups present are $C(Y)_2COOZ$, with a further provisio that if Z is Mn(II), two Z containing X groups share one Mn(II).

The X group not being $C(Y)_2COOZ$ is an alkyl group or a linker.

The term "alkyl" by itself or as a part of another substituent refers to a hydrocarbon, preferably a lower alkyl, for instance a $C_1$-$C_6$ alkyl and more preferably —CH$_3$.

The term PEG means polyethylene glycol of any molecular weight. Preferably 1 to 5 kD PEG units.

Y can preferably be methyl, —COOH, —PO(OH)$_2$, —H or a linker. Most preferably Y is —H or a linker.

R can preferably be methyl, —NMe$_2$, —NH$_2$, —OMe, —OH or a linker. Most preferably R is a linker.

The linker, if present, attaches the compound of formula (I) to another molecule. The choice of said another molecule will effect the biodistribution and signal properties of the contrast agent.

Preferably the linker moiety can be selected from the group comprising:

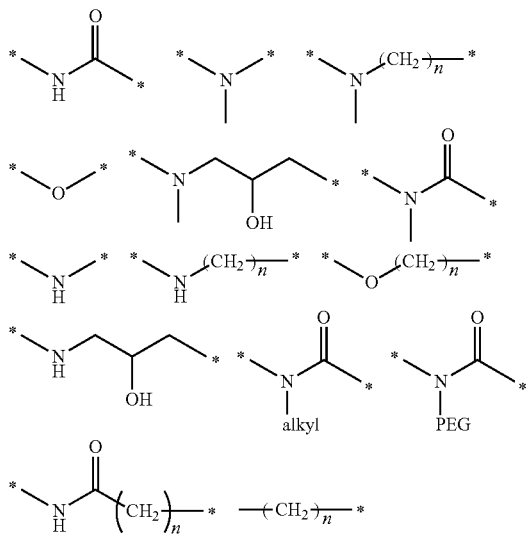

wherein n is an integer from 1 to 7
* denotes the position whereby the linker is attached to the compound of formula (I) and the other molecule defined above.
Preferably the linker is selected from the group

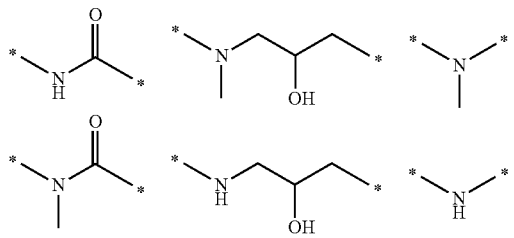

Most preferably, the linker is

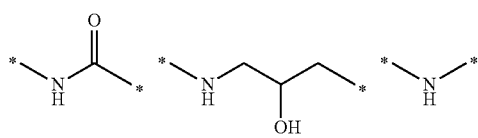

Hence, a preferred embodiment of a compound of formula (I) is a compound of formula (II)

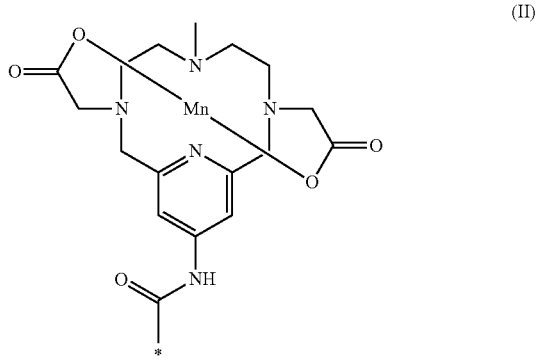

where * indicate the attachment point to said another molecule.
In this embodiment one X is $CH_3$, one X is $C(Y)_2COOZ$, and one X is $C(Y)_2COO^-$, Z is Mn(II), Y is —H and the linker is:

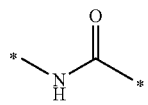

Compounds of the present invention can be used as MR contrast agents, and as explained above, may or may not be attached to other molecules such as natural or synthetic peptides, amino acids or derivatives thereof, polyamines or derivatives thereof, peptidomimetics, polypeptides, proteins or antibodies. By linking compounds of the present invention to these molecules, targeted MR contrast agents may be obtained if the for instance peptide or protein is a vector which binds to a target like a receptor or cell surface marker. Further, compounds of the present invention may be attached to polymeric moieties such as natural or synthetic polymers or dendrimers. Such a linking gives compounds of the present invention a further reduced molecular mobility and therefore increase its relaxivity at high field strengths used in modern MRI scanners. In another embodiment compounds of the present invention may be attached to lipophilic compounds and the resulting amphiphilic compounds may be dispersed. Such dispersions may be used as MR contrast agent for tumour imaging. In yet another embodiment the compounds of the present invention may be attached to nanoparticles. Again such a linking gives compounds of the present invention a further reduced molecular mobility and therefore increases their relaxivity.

Therefore, in a second aspect of the invention there is provided a compound of formula (I) as defined above attached to another molecule via the, X, Y or R group. In this context the term 'another molecule' includes atoms. In a preferred embodiment, said another molecule is O, S, P or N, most preferably N. In another preferred embodiment, said another molecule is an aromatic ring, inositol or carbohydrate, or any derivative thereof. In another preferred embodiment, said another molecule is a natural or synthetic peptide, amino acids or derivatives thereof, polyamines or derivatives thereof, a peptidomimetic, a polypeptide, a protein, an antibody, a natural or synthetic polymer, a dendrimer, a nanoparticle or a lipophilic compound. By attaching compounds of formula (I) to other molecules, the biodistribution will be altered and the contrast agent can be internalized or bound to cells with an affinity for the molecule attached to the compound of formula (I).

It is apparent to the skilled person that the linker moiety of X, Y or R group can be attached to other molecules by any method known in the art.

In one preferred embodiment, compounds of the present invention are attached to a dendrimer. A dendrimer is a repeatedly branched molecule and will serve as a scaffold for the attachment of a multiplicity of compounds of formula (I). In its simplest form a dendrimer may consist of a core scaffold only but allow for the attachment of a multiplicity of compounds of formula (I). Dendrimeric constructs will have an altered biodistribution and enhanced signal compared to monomeric chelates.

Suitable dendrimeric compounds incorporating compounds of formula (I) are 5 6
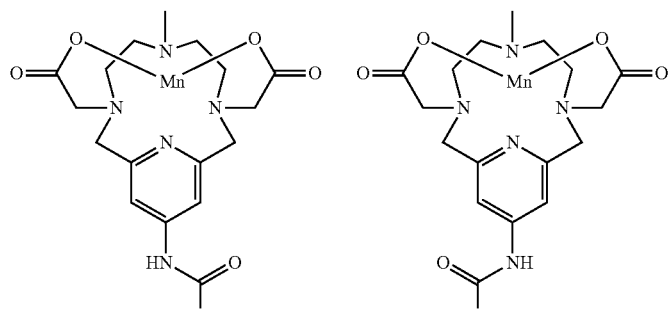
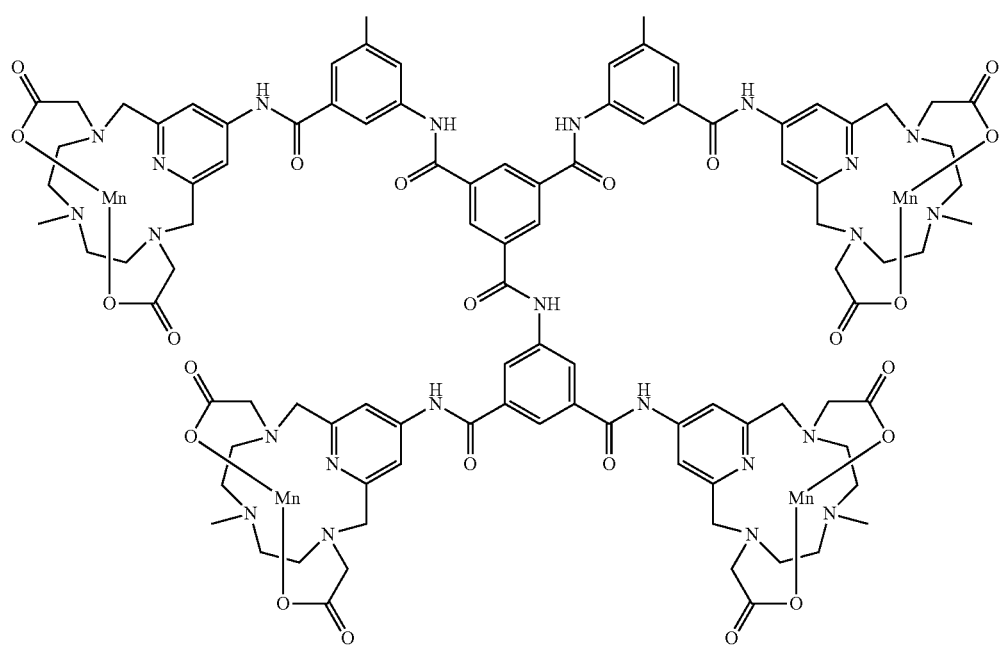
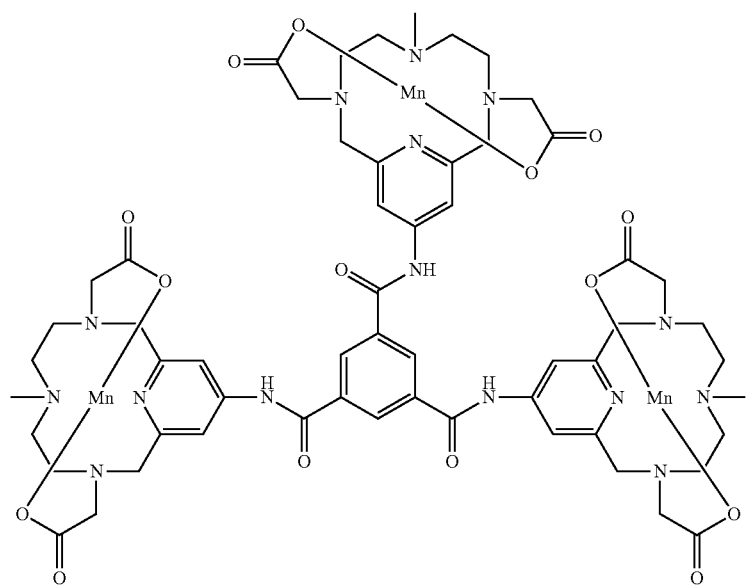

-continued
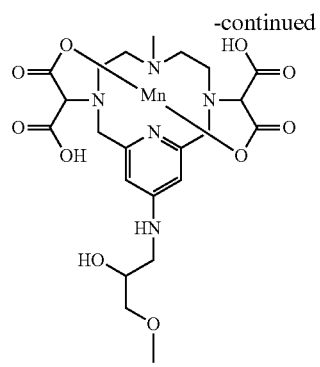
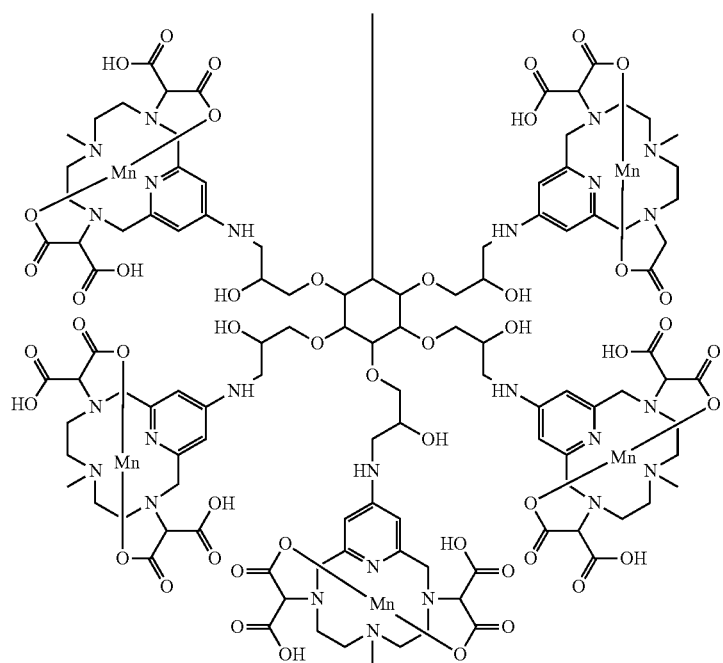
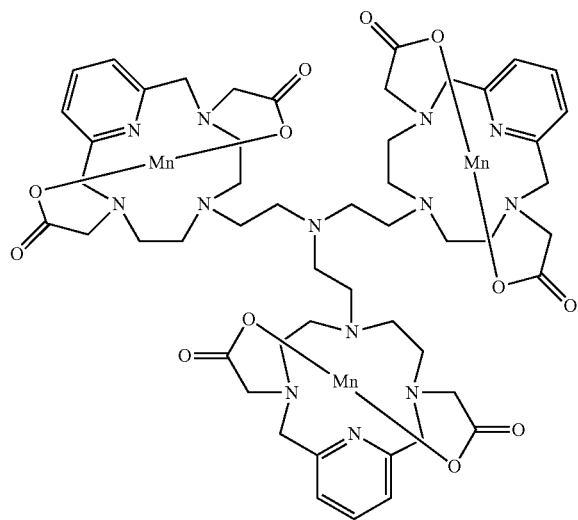

Suitable derivatives of natural or synthetic peptides, amino acids derivatives thereof, polyamines and derivatives thereof, peptidomimetics, or polypeptides, incorporating compounds of formula (I) are:

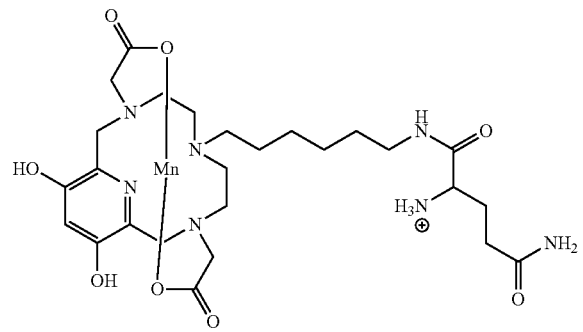

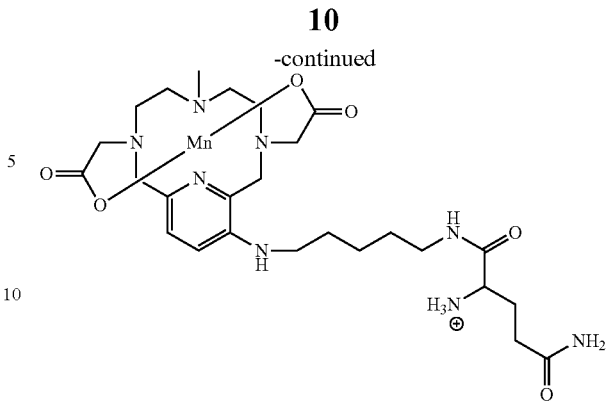

In the case said other molecule is a receptor ligand moiety associated with malignant tumors, R cannot be a linker containing a $C_2$-$C_{10}$ hydroxycarbylene chain.

The compounds of formula (I) can be synthesized by several synthetic pathways known to the skilled artisan from commercially available starting materials by the following generalized procedure.

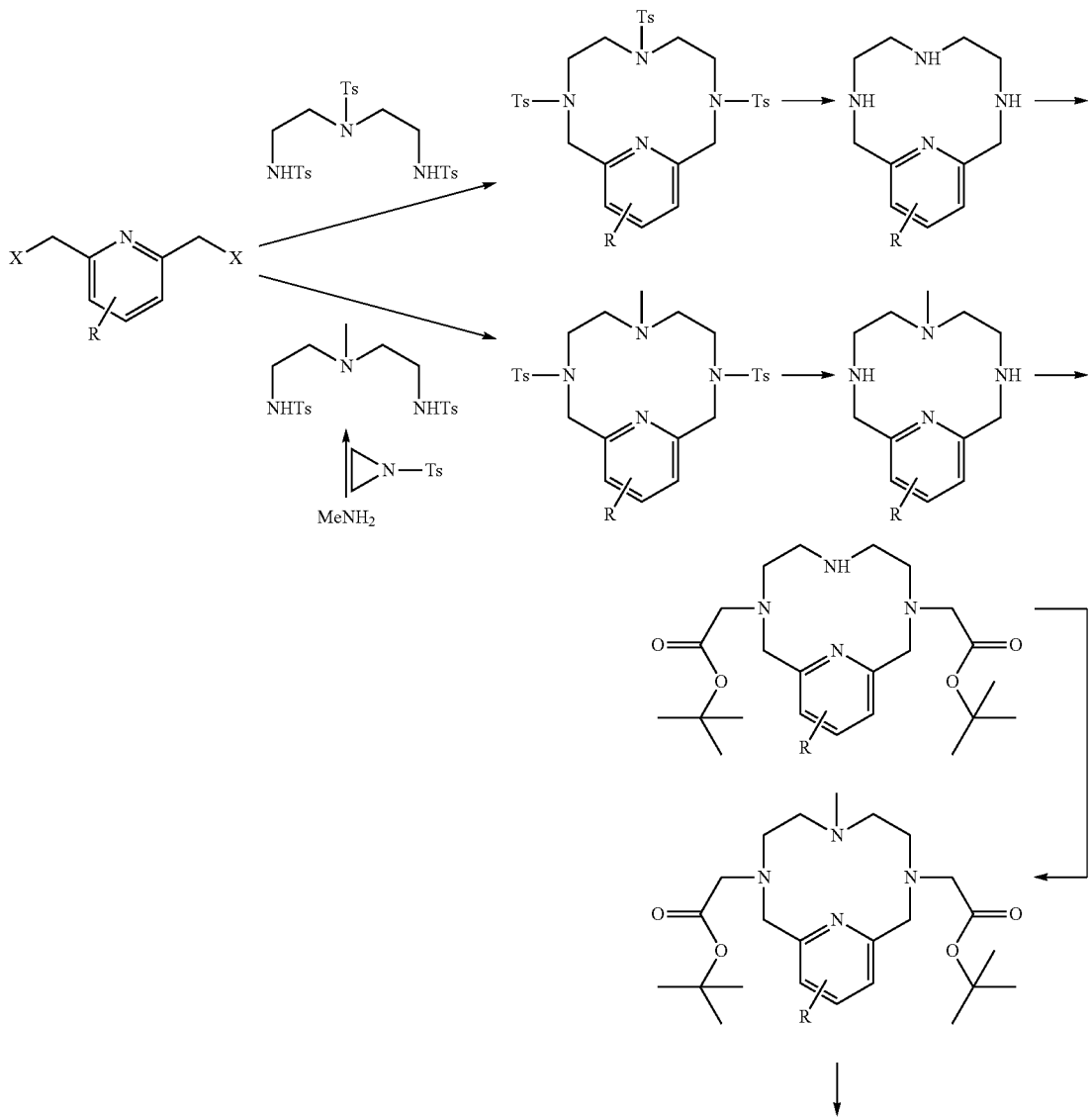

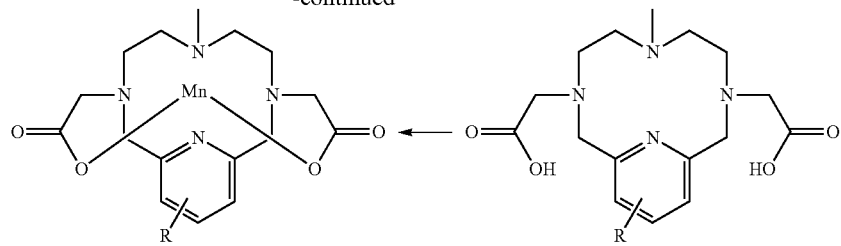

A 2,6-bis-methyl-pyridine compound equipped with leaving groups (X) at the methyl positions can be obtained from commercially available materials by methods well known to those of skill in the art. Examples of suitable leaving groups are chloro-, bromo-, tosyl-nosyl- and mesyl-groups. The pyridine ring may be substituted with a group (R) that can be used as an attachment point if the chelate is to be coupled to another molecule. An example of a suitable R group is —$NH_2$. The R group can also be an inert precursor to the group utilized in the subsequent coupling reaction, i.e. the —$NO_2$ group is a precursor to the —$NH_2$ group. One can also envision R groups with the sole function of increasing the stability of the subsequent manganese complex, by electronic delocalization to the pyridine nitrogen. Examples of such R groups are —$CH_3$ and —$OCH_3$. The 2,6-bis-methyl-pyridine compound equipped with suitable leaving groups, as defined above, is then cyclized by reaction with a suitable bis-amino nucleophile to form a tetraazamacrocycle by methods well known to those of skill in the art. The nucleophilic nitrogens can be equipped with tosylate groups that favour the cyclization reaction as known by those skilled in the art. The subsequent removal of the tosylate groups can be performed by methods known in the art. The introduction of two carboxymethyl groups to two of the three aliphatic nitrogens can be accomplished by careful regioselective alkylation, preferably performed under strict pH control by methods well known to those of skill in the art. The remaining secondary nitrogen can subsequentely be alkylated by a carbon electrophile. Examples of such carbon electrophiles are $CH_3I$ and $CF_3SO_2OCH_3$. The alkyl group can also be introduced prior to the cyclization reaction by reacting an alkylated bis-tosylamide derivative with the electrophilic pyridine compound. An early introduction of the alkyl group obliviates the need for a regioselective introduction of carboxymethyl groups in a subsequent reaction step. The carboxymethyl groups can be protected in an ester form. This is especially useful when the cheland is to be coupled to another molecule, by reaction of the R group using methods well known to those of skill in the art, as the solubility in solvents, useful for the coupling reaction, is dramatically reduced for the free carboxylic acid derivative. Examples of such ester groups are t-butyl, ethyl and methyl esters. The removal of ester groups is well known to those of skill in the art. The complexation can be performed in aqueous solution by reaction using a suitable source of manganese(II) ion using methods well known to those of skill in the art.

Compounds of the present invention attached to other molecules via the X, Y or R group can be prepared by methods known in the art. If for instance said other molecule is a peptide, polypeptide or protein, compounds of formula (I) can be readily attached to suitable functional groups in said other molecules, e.g. carboxyl groups. It may be necessary to activate the functional groups in said other molecules, e.g. generating an acyl chloride from a carboxyl group. Methods to activate functional groups in order to enhance their reactivity are known to the skilled person in the art (see for example Sandler and Karo, eds. Organic Functional Group preparation, Academic Press, San Diego 1998).

Compounds of formula (I) and compounds of formula (I) attached to other molecules, preferably to natural or synthetic peptides, amino acids and derivatives thereof, polyamines and derivatives thereof, peptidomimetics, polypeptides, proteins, antibodies, natural or synthetic polymers, dendrimers, lipophilic compounds or nanoparticles may be used as MR contrast agents. Thus, a third aspect of the present invention provides compounds for use as MR contrast agents.

For this purpose, the compounds of formula (I) and compounds of formula (I) attached to other molecules are formulated with conventional physiologically tolerable carriers like aqueous carriers, e.g. water and buffer solutions, and optionally with excipients. The resulting composition is denoted "MR contrast medium".

A fourth aspect the invention provides a composition comprising a compound of formula (I) or a compound of formula (I) attached to other molecules and at least one physiologically tolerable carrier. Said composition may be used as MR contrast medium in MRI.

To be used as MR contrast medium in MRI of the human and non-human animal body, said MR contrast medium needs to be suitable for administration to said body. Suitably, the compounds of formula (I) or compounds of formula (I) attached to other molecules and optionally pharmaceutically acceptable excipients and additives may be suspended or dissolved in at least one physiologically tolerable carrier, e.g. water or buffer solution(s). Suitable additives include for example physiologically compatible buffers like tromethamine hydrochloride, chelators such as DTPA, DTPA-BMA or compounds of formula (I), weak complexes of physiologically tolerable ions such as calcium chelates, e.g. calcium DTPA, CaNaDTPA-BMA, compounds of formula (I) wherein X forms a complex with Ca2+ or Ca/Na salts of compounds of formula (I), calcium or sodium salts like calcium chloride, calcium ascorbate, calcium gluconate or calcium lactate. Excipients and additives are further described in e.g. WO-A-90/03804, EP-A-463644, EP-A-258616 and U.S. Pat. No. 5,876,695, the content of which are incorporated herein by reference.

A fifth aspect of the invention is a method of MR imaging wherein a composition comprising a compound of formula (I) or a compound of formula (I) attached to another molecule and at least one physiologically tolerable carrier is administered to a subject and the subject is subjected to an MR examination wherein MR signals are detected from the subject or parts of the subject into which the composition distributes and optionally MR images and/or MR spectra are generated from the detected signals. In a preferred embodiment, the subject is a living human or non-human animal body.

In a preferred embodiment, the composition is administered in an amount which is contrast-enhancing effective, i.e. an amount which is suitable to enhance the contrast in the method of MR imaging.

In another preferred embodiment, the subject is a living human or non-human animal being and the method of MR imaging is a method of MR tumour detection or a method of tumour delineation imaging.

In a sixth aspect, the invention provides a method of MR imaging wherein a subject which had been previously administered with a composition comprising a compound of formula (I) or a compound of formula (I) attached to another molecule and at least one physiologically tolerable carrier is subjected to an MR examination wherein MR signals are detected from the subject or parts of the subject into which the composition distributes and optionally MR images and/or MR spectra are generated from the detected signals.

The term "previously been administered" means that any step requiring a medically-qualified person to administer the composition to the patient has already been carried out before the method of MR imaging and/or MR spectroscopy according to the invention is commenced.

In a seventh aspect, the invention is related to the use of a compound according to the invention for the manufacture of a diagnostic agent for use a MR contrast medium.

The invention will now be described in greater detail by way of the following non-limiting examples.

EXAMPLES

Example 1 a) Synthesis of 3,6,9-tris-(toluene-4-sulfonyl)-3,6,9,15-tetraaza-bicyclo[9.3.1]pentadeca-1(14),11(15),12-triene

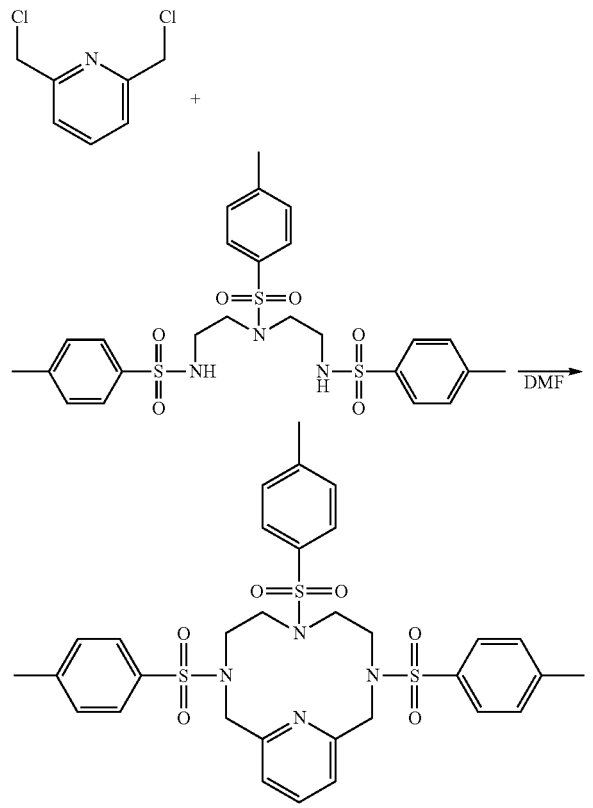

N,N',N"-Tri-p-tosyldiethylene-triamine disodium salt (6.90 g, 11.4 mmol) in dimethylformamide (DMF) (92 mL) was heated to 100° C. under N$_2$-atm. 2,6-Bis(chloromethyl) pyridine (2.01 g, 11.4 mmol) in DMF (37 mL) was added dropwise over 45 min. When the addition was completed the reaction mixture was stirred at 40° C. under N$_2$-atm for 12 hours. To the reaction mixture was then added 75 mL water. The resulting slurry was then filtered and the solid washed with water and dried in vacuo. The crude product was attempted dissolved in water:acetonitrile 1:1. A white precipitate was filtered off and dried affording 5.52 g (72%) of the product.

The product was analysed using LC-MS (found m/z: 669.3 MH+, calculated m/z: 669.2).

b) Synthesis of the HBr salt of 3,6,9,15-tetraaza-bicyclo[9.3.1]pentadeca-1(14),11(15),12-triene

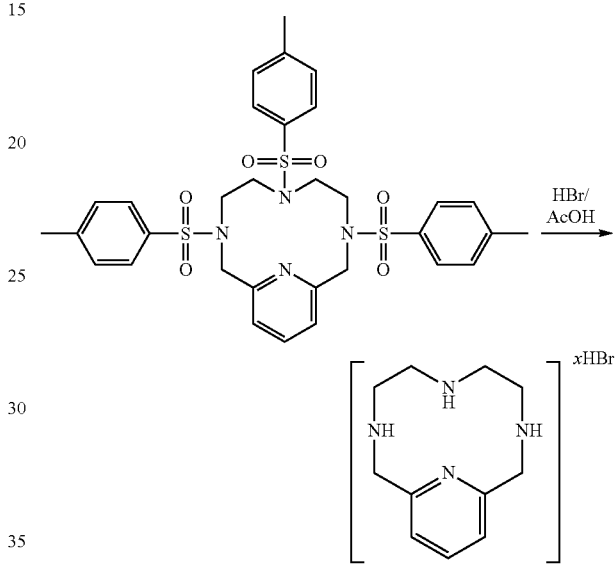

A solution of HBr and acetic acid was prepared by mixing 48% HBr and glacial acetic acid in a 65:35 ratio. To 111 mL of the HBr/AcOH mixture was added the product obtained in step 1a (5.0 g, 7.5 mmol) and the reaction mixture was heated at mild reflux with constant stirring for 80 hours. The reaction mixture was then cooled to room temperature and concentrated to approximately 1/10 of the original volume. The remaining mixture was stirred vigorously and 50 mL of diethyl ether was added. The formed off-white solid was filtered, washed with diethyl ether and dried in vacuo affording 3.8 g of crude product. The crude product was used without purification. The crude product was analysed using LC-MS (found m/z: 207.3 MH+, calculated m/z: 207.2).

c) Synthesis of 3,6,9,15-tetraaza-3,9-bis-(tert-butyl-carbonylmethyl)-bicyclo[9.3.1]pentadeca-1(14),11(15),12-triene

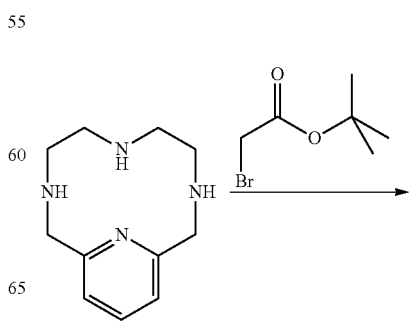

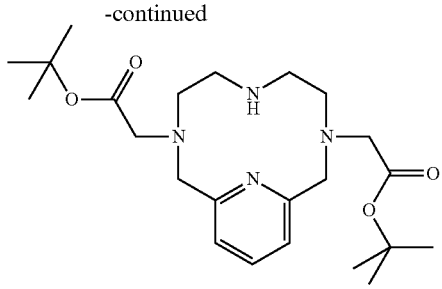

The compound obtained in step 1b (1.5 g, 3.3 mmol) was dissolved in dioxane:water 1:1 (30 mL) and pH was adjusted to 3 with NaOH (2 M) before tert-butylbromo acetate (0.66 mL, 4.5 mmol) in dioxane:water (35 mL) was added. pH after addition was adjusted to 9 with NaOH (2 M). After 3.5 hours more tert-butylbromo acetate (0.10 mL, 0.68 mmol) was added and the pH was adjusted to 9 with NaOH (2 M). The addition of more tert-butylbromo acetate was repeated twice (2×0.116 mL, 0.79 mmol) after 14 and 17 hours. The pH was also adjusted to 9. The reaction mixture was loaded onto C18 preparative column and the product was purified using preparative HPLC. 0.9 g (63%) of pure compound was isolated.

The product was analysed using LC-MS (found m/z: 435.1 MH+, calculated m/z: 435.3).

d) Synthesis of 3,6,9,15-tetraaza-3,9-bis-(tert-butyl-carbonylmethyl)-6-methyl-bicyclo[9.3.1]pentadeca-1(14),11(15),12-triene

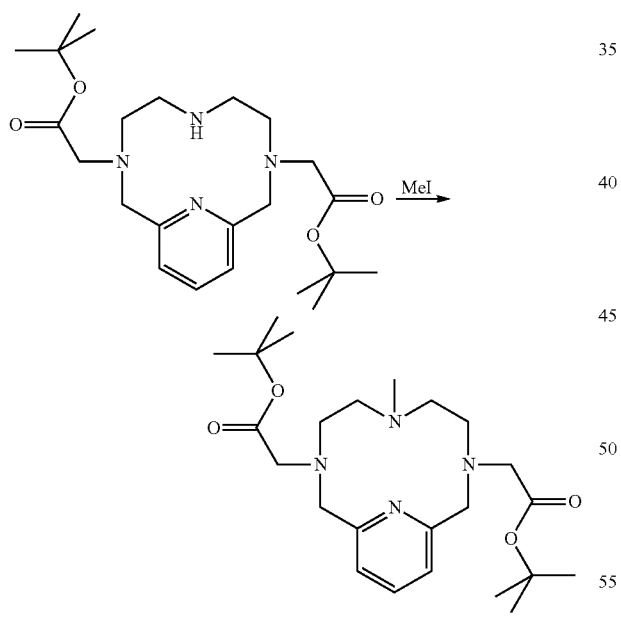

To the compound obtained in step 1c (200 mg, 0.460 mmol) in dimethylformamide (10 mL) was added triethyl amine (65.3 mg, 64.1 µL, 0.460 mmol) and iodometane (65.3 mg, 28.7 µL, 0.460 mmol). Aliquots of 1,1,3,3-tetramethylguanidine (58 µL, 0.46 mmol) and iodomethane (29 uL, 0.46 mmol) was added. The reaction was followed using LC-MS and then water was added. The reaction mixture purified by preparative HPLC. 106 mg, 0.24 mmol (51%) of pure compound was isolated.

The product was analysed using LC-MS (found m/z: 449.1 MH+, calculated m/z: 449.3).

e) Synthesis of 3,6,9,15-tetraaza-3,9-bis-(carboxymethyl)-6-methyl-bicyclo[9.3.1]pentadeca-1(14),11(15),12-triene

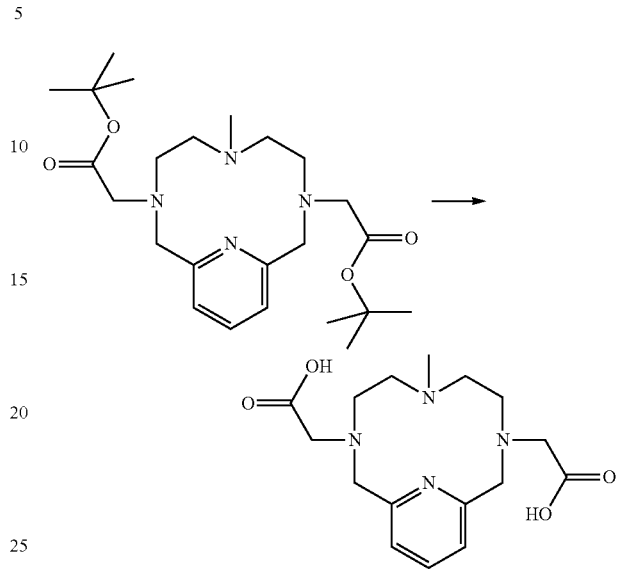

The compound obtained in step 1d (0.11 g, 0.24 mmol) in formic acid (30 mL) was heated to reflux and cooled to room temperature. Formic acid was evaporated under reduced pressure. Toluene (2×20 mL) was added and evaporated under reduced pressure. The crude product was used in the next step without purification.

The product was analysed using LC-MS (found m/z: 337.1 MH+, calculated m/z: 336.2).

f) Synthesis of the manganese(II) complex of 3,6,9,15-tetraaza-3,9-bis-(carboxymethyl)-6-methyl-bicyclo[9.3.1]pentadeca-1(14),11(15),12-triene

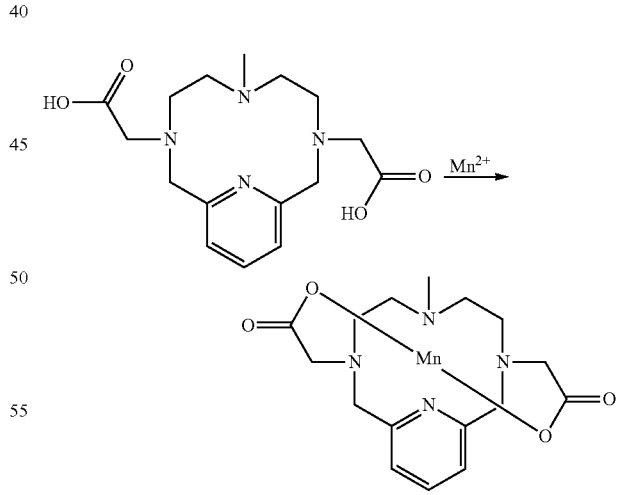

The compound obtained in step 1e (81 mg, 0.24 mmol) was dissolved in degassed water (15 mL) before pH was adjusted from 2.8 to 6.7 using 200 µL NaOH in degassed water (2.35 M). 1.1 mL of manganese(II) chloride in degassed water (465 mg in 10 mL, 0.23 M) was added. pH dropped to 3.5. pH was adjusted to 5.9 with aliquots of NaOH (aq). After 15 minutes the pH was adjusted to 9.3 with aliquots of NaOH (aq) and the mixture left for 15 minutes. The pH was adjusted to 7.0 using aliquots of HCl (150 μL in 1 mL degassed water) before the solution was filtered and loaded onto a C18 preparative column and the product was purified using preparative HPLC. 0.11 mmol, 42 mg (45%) of pure compound was isolated.

The product was analysed using LC-MS (found m/z: 390.0 MH+, calculated m/z: 390.1).

Example 2 a) Synthesis of dimethyl 4-aminopyridine-2,6-dicarboxylate

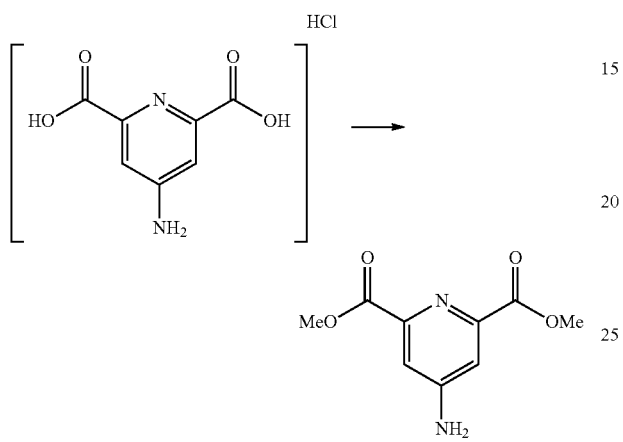

Thionyl chloride (2.5 mL) was slowly added to ice cooled methanol (20 mL) under a nitrogen atmosphere. Then the hydrochloric salt of 4-aminopyridine-2,6-dicarboxylic acid (2.5 g, 11.5 mmol) was added batchwise to ice cooled solution. Then the reaction mixture was refluxed for 4 h and was then concentrated to give a yellow amorphous solid. The solid was dissolved in aqueous HCl (0.8M, 50 mL) and the solution was filtered and basified to pH 9. The formed precipitate was filtered off to give the wanted product (1.6 g, 66%). The product was analysed using NMR ((CD$_3$)$_2$SO), 7.36 (s, 2H), 6.70 (bs, 2H), 3.84 (s, 6H)).

b) Synthesis of (4-aminopyridine-2,6-diyl)dimethanol

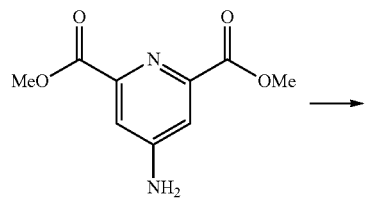

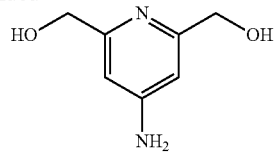

To the compound obtained in step 2a (2.8 g, 13.3 mmol) was added methanol (100 mL). Batchwise addition of sodium borohydride caplets (a total of 4 g, 11 mmol) over 1 h gave a clear solution. Reaction mixture was then refluxed and additional sodium borohydride caplets (additional 4 g, 11 mmol) were added batchwise for 1 h. Then water (25 mL) was added and the reaction mixture was concentrated to give a white amorphous powder. The solids were subjected to soxhlet extraction in ethyl acetate for 72 h. The organic phase was then concentrated and water (100 mL) was added. The pH was adjusted to 11 and the resulting slurry was heated at 75° C. for 1 h to give a clear solution. The pH was the adjusted to 12 and the solution was cooled to 0° C. The formed precipitate was filtered off to give the wanted product as an amorphous solid (1.3 g, 66%). The product was analysed using LC-MS (found m/z: 155.1 MH+, calculated m/z: 155.1).

c) Synthesis of 2,6-bis(chloromethyl)pyridin-4-amine

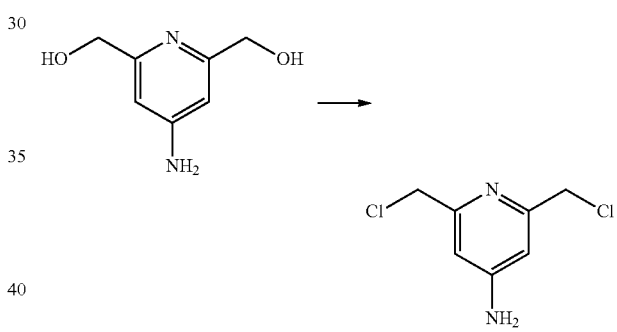

To the compound obtained in step 2b (2.3 g, 14.9 mmol) was added thionyl chloride (15 mL) and then the resulting foaming gel was refluxed for 2 h. Then the reaction mixture was concentrated to give an amorphous solid to which was added water (30 mL). The resulting slurry was basified to pH 8 and the precipitate was filtered off to give wanted product (2.6 g, 88%). The product was analysed using LC-MS (found m/z: 191.0 MH⁺, calculated m/z: 191.0).

d) Synthesis of 13-amino-3,6,9,15-tetraaza-3,9-bis-(toluene-4-sulfonyl)-6-methyl-bicyclo[9.3.1]pentadeca-1(14),11(15),12-triene

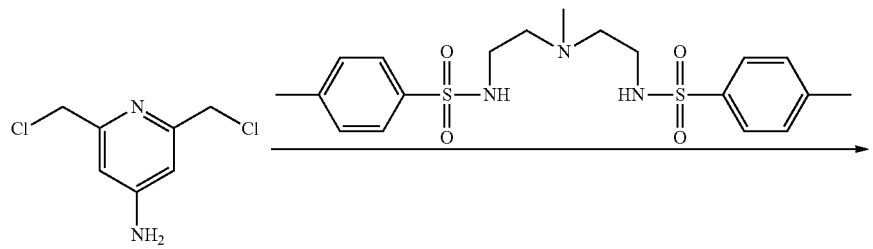

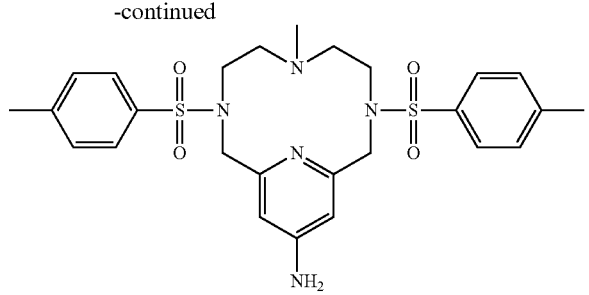

To the compound obtained in step 2c (2.5 g, 13.1 mmol), N,N'-(2,2'-(methylazanediyl)bis(ethane-2,1-diyl))bis(4-methylbenzenesulfonamide) (2.8 g, 6.6 mmol) and K$_2$CO$_3$ (11 g, 79.7 mmol) was added dimethyl formamide (250 mL). The resulting slurry was stirred at 100° C. under a nitrogen atmosphere for 2 h. Then additional N,N'-(2,2'-(methylazanediyl)bis(ethane-2,1-diyl))bis(4-methylbenzenesulfonamide) (2.8 g, 6.6 mmol) was added and heating was continued for 4 h. Then 125 mL of dimethyl formamide was evaporated off and the remaining slurry was added dropwise to a vessel containing water (1.6 L). The resulting slurry was acidified to pH 1 and was then heated to 75° C. The solution was allowed to cool to room temperature aver night and the resulting precipitate was filtered off to give wanted product (5.1 g, 72%). The product was analysed using LC-MS (found m/z: 544.1 MH$^+$, calculated m/z: 544.2).

e) Synthesis of 13-amino-3,6,9,15-tetraaza-3,9-bis-(tert-butylcarbonylmethyl)-6-methyl-bicyclo[9.3.1]pentadeca-1(14),11(15),12-triene

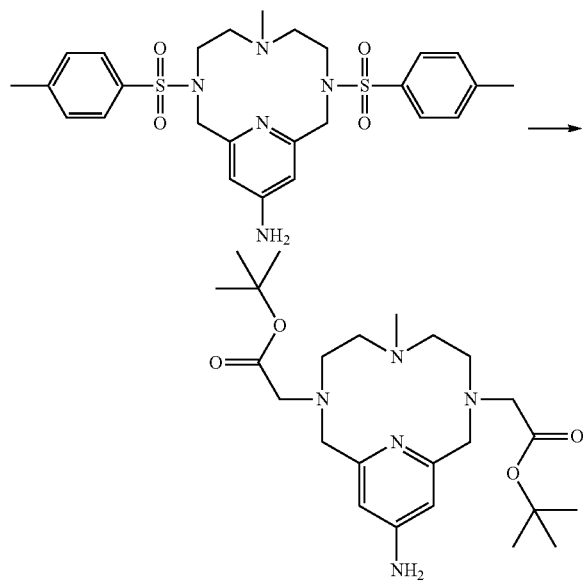

To the compound obtained in step 2d (2.5 g, 4.6 mmol) was added concentrated sulphuric acid (15 mL). The resulting slurry was stirred at 100° C. for 8 h and was then crashed into ice cooled water (40 mL). Then an aqueous solution of NaOH (25%, 90 mL) was added to give a white slurry. To slurry was added acetonitrile (50 mL), K$_2$CO$_3$ (1.2 g, 8.7 mmol) and tert-butylbromoacetate (1.36 mL, 9.2 mmol). The biphasic slurry was stirred vigorously for 5 h and then additional tert-butylbromoacetate (1.36 mL, 9.2 mmol) was added. After 12 h the organic phase was separated and added to a buffer solution (0.1M NaHCO$_3$/Na$_2$CO$_3$ at pH 10) solution saturated with NaCl. To the biphasic solution was added tert-butylbromoacetate (1.36 mL, 9.2 mmol) and then the mixture was stirred vigorously for 24 h. Then additional tert-butylbromoacetate (1.36 mL, 9.2 mmol) was added and the mixture was stirred vigorously for 24 h. The organic phase was separated and added to a phosphate buffer (300 mL, 0.1M, pH 7). The aqueous solution was then extracted repeatedly with dichloromethane. The combined organic phases were dried with magnesium sulphate, filtered and concentrated to give wanted product (2.7 g). The product was analysed using LC-MS (found m/z: 464.2 MH$^+$, calculated m/z: 464.3).

f) Synthesis of the manganese(II) complex of N1,N3,N5-tris[3,6,9,15-tetraaza-3,9-bis-(carbonylmethyl)-6-methyl-bicyclo[9.3.1]pentadeca-13-trienyl]benzene-1,3,5-tricarboxamide

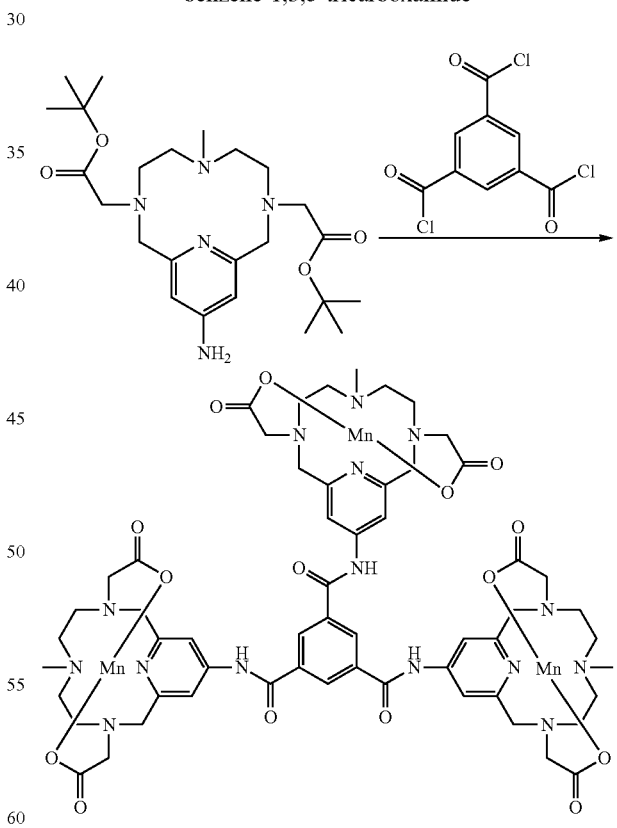

The compound obtained in step 2e (1.0 g, 1.1 mmol) was dissolved in acetonitrile (10 mL), then N-ethyldiisopropylamine (185 uL, 1.1 mmol) and benzene tricarboxylic acid chloride (64 uL, 0.36 mmol) was added and reaction mixture was stirred at room temperature for 1 h. The reaction mixture was then concentrated to give a white amorphous solid. The solid was then dissolved in formic acid (10 mL) and heated to reflux for 1 h. The reaction mixture was then concentrated and the resulting material was dissolved in saturated NaHCO$_3$ buffer and was heated at 80° C. for 24 h. The reaction mixture was neutralized and then MnCl$_2$ (435 mg, 2.2 mmol) was added. pH was then adjusted to 7.6 and stirred at room temperature for 1 h. Reaction mixture was then filtered and concentrated. Preparative HPLC gave trimeric manganese(II) complex (230 mg, 47% over three steps). The product was analysed using LC-MS (found m/z: 457.0 M3H$^+$, calculated m/z: 457.1).

Example 3

Relaxivity Analysis

The relaxivity measurements were performed with a range of 0.05 to 1 mM complex solutions on a Bruker Minispec PC 120b-NA 770, at 20 MHz or a Bruker Minispec Mq 60m at 60 MHz and 37° C. The solutions were obtained by dissolving the appropriate amount of chelate in degassed Millipore water or human serum.

Water Exchange Measurements

The water exchange measurements were performed with 6 to 15 mM complex solutions. The solutions were obtained by dissolving the appropriate amount of complex in 0.6 mL of buffer solution (TRIS, 0.05 M, pH 7.4 in degassed Millipore water at ca. 3 atom % $^{17}$O-enrichment); Variable-temperature Fourier transform $^{17}$O NMR spectra were recorded at a frequency of 40.7 MHz on a Varian Unity 300 MHz spectrometer. The temperatures were measured using methanol and ethylene glycol standards. The temperature dependence of the $^{17}$O line broadening for each system was measured over a temperature range from 273.7 to 356.1 K. Each temperature was calibrated using a methanol or ethylene glycol standard.

| Compound | Relaxivity Water @ 20 MHz, 37° C. (mM$^{-1}$s$^{-1}$) | Relaxivity Human Serum @ 60 MHz, 37° C. (mM-1s-1) | Water residence time (ns) |
|---|---|---|---|
| Compound of Example 1 | 2.4 | 4.6 | 16 |
| Compound disclosed in US5334371 | 1.3 | NA | NA |
| Compound of Example 6 | NA | 8.8 | NA |

| Compound | Relaxivity Water @ 20 MHz, 37° C. (mM$^{-1}$s$^{-1}$) | Relaxivity Human Serum @ 60 MHz, 37° C. (mM-1s-1) | Water residence time (ns) |
|---|---|---|---|
| 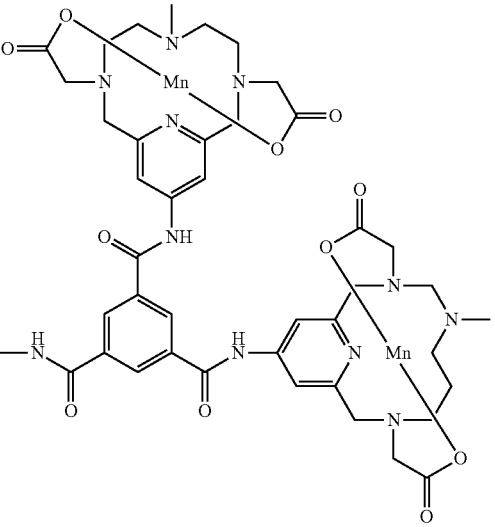 Compound of Example 2 | 3.8 | 10.5 | 14 |

Example 4

Stability Analysis

The kinetic stability of manganous chelates was characterized by the rates of exchange reaction with $Zn^{2+}$, in acetate buffer (10 mM) set to various pH. The increase of free manganous ions was monitored using a Bruker Minispec PC 120b-NA 770, at 20 MHz and 25° C. The total ionic strength was adjusted to 0.5M with KCl. The chelate concentration was approximately 0.5 mM for all measurements.

The change in concentration of chelated manganese, upon challenge with zinc ions, was monitored spectroscopically. When zinc displaces a manganous ion a net increase in relaxivity was observed as the free manganous ion has a relaxivity of ~10 mM$^{-1}$s$^{-1}$, whereas the studied manganese chelates have a lower relaxivity.

The pseudo first-order rate constants ($k_{obs}$) were calculated by fitting the relaxivity data to the following equation:

$$A_t = (A_0 + A_e)e^{(k_{obs}t)} + A_e$$

in which $A_t$, $A_0$, and $A_e$ are the relaxivity values at time t, the start of the reaction, and at equilibrium, respectively. The dissociation half life was derived from $k_{obs}$.

| pH | [Zn] (mM) | Compound of example 1 Dissociation Half life $t_{1/2}$ (min) | Compound disclosed in US 5334371 Dissociation Half life $t_{1/2}$ (min) |
|---|---|---|---|
| 5.6 | 10 | 72 | 22 |
| 5.4 | 10 | 44 | 15 |
| 5.2 | 10 | 30 | 9 |
| 5.0 | 10 | 21 | 6 |
| 4.6 | 10 | 10 | 3 |
| 5.6 | 20 | 77 | 23 |
| 5.2 | 20 | 37 | 10 |

Example 5 a) Synthesis of N,N',N'',N''',N'''',N'''''-(((nitrilotris(ethane-2,1-diyl))tris(azanetriyl))hexakis(ethane-2,1-diyl))hexakis(4-methylbenzenesulfonamide)

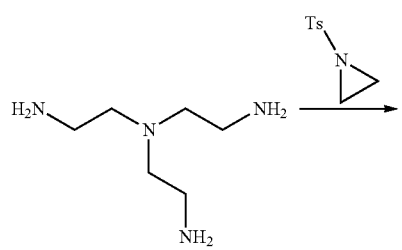

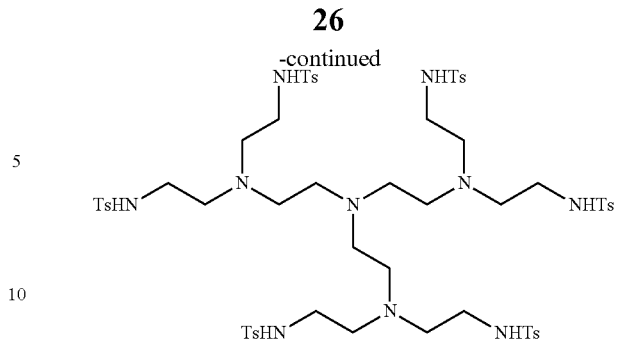

tris-(2-aminoethyl)-amine (10 g, 68.5 mmol) is dissolved in acetonitrile (500 mL) and then tosylaziridine (97.2 g, 0.49 mol) is added slowly. The solution is stirred for 24 at room temperature then NaOH (2.7 g, 68.5 mmol) is added and stirring is continued for another 24 h. The reaction mixture is then crashed into water (2 L) and the resulting precipitate is filtered off to give pure product.

b) Synthesis of 6,6',6''-tris-ethyl-[3,6,9,15-tetraaza-3,9-bis-(4-methylbenzenesulfonamide)-bicyclo[9.3.1]pentadecatrien]-amine

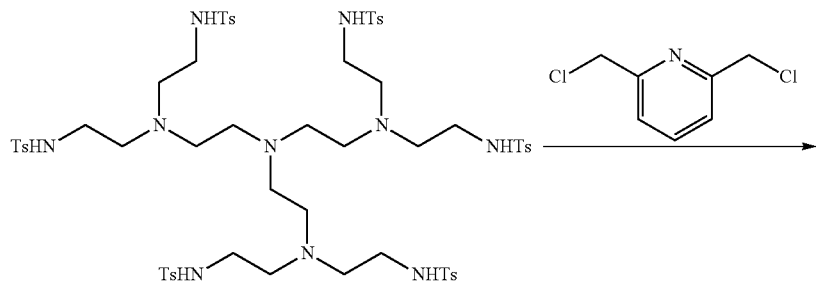

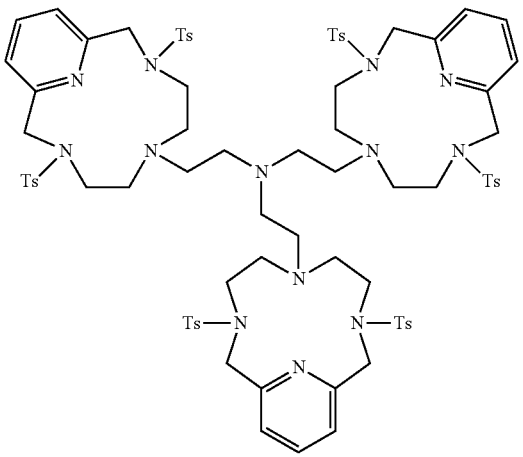

The compound obtained in example 5a (10 g, 7.5 mmol) is dissolved in DMF (200 mL) and then 2,6-bis(chloromethyl)pyridine (8.1 g, 46 mmol) and potassium carbonate (12.7 g, 92 mmol) is added. The reaction mixture is heated to 80° C. for 24 h and is then crashed into water (1 L). The precipitate is filtered off to give pure product.

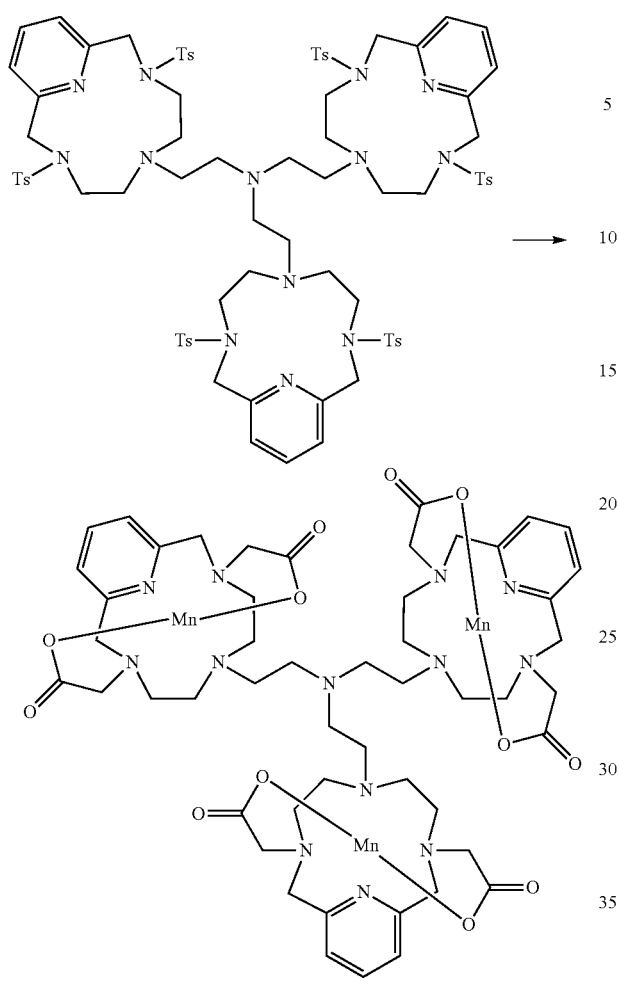

c) Synthesis of Manganese complex of 6,6',6"-tris-ethyl-[3,6,9,15-tetraaza-3,9-bis-(carbonylmethyl)-bicyclo[9.3.1]pentadecatrien]-amine To the compound obtained in example 6b (10 g, 6.1 mmol) is added concentrated sulphuric acid (50 mL) and the resulting slurry is heated at 100° C. for 12 h and then crashed into ice cooled water (1 L). Then an aqueous solution of NaOH (25%, 300 mL) is added to give a white slurry. To the slurry is added acetonitrile (400 mL), $K_2CO_3$ (5.1 g, 37 mmol) and tert-butylbromoacetate (22.2 mL, 0.15 mol). The biphasic slurry is stirred vigorously for 15 h and then the organic phase is separated and added to a phosphate buffer (1 L, 0.1M, pH 7). The aqueous solution is then extracted repeatedly with dichloromethane. The combined organic phases is concentrated to give an amorphous solid. The solid is dissolved in formic acid (50 mL) and refluxed for 5 h. The reaction mixture is the concentrated and the resulting amorphous solid is dissolved in water (100 mL), neutralized and then $MnCl_2$ (3.5 g, 27.5 mmol) is added. pH is then adjusted to 7.6 and the reaction mixture is stirred at room temperature for 1 h. Reaction mixture is then filtered and concentrated. The amorphous solid is crystallized from refluxing ethanol to give manganese complex of 6,6',6"-tris-ethyl-[3,6,9,15-tetraaza-3,9-bis-(carbonylmethyl)-bicyclo[9.3.1]pentadecatrien]-amine.

Example 6 a) Synthesis of N,13-Benzamide-3,6,9,15-tetraaza-3,9-bis-(tert-butylcarbonylmethyl)-6-methyl-bicyclo[9.3.1]pentadeca-1(14),11(15),12-triene

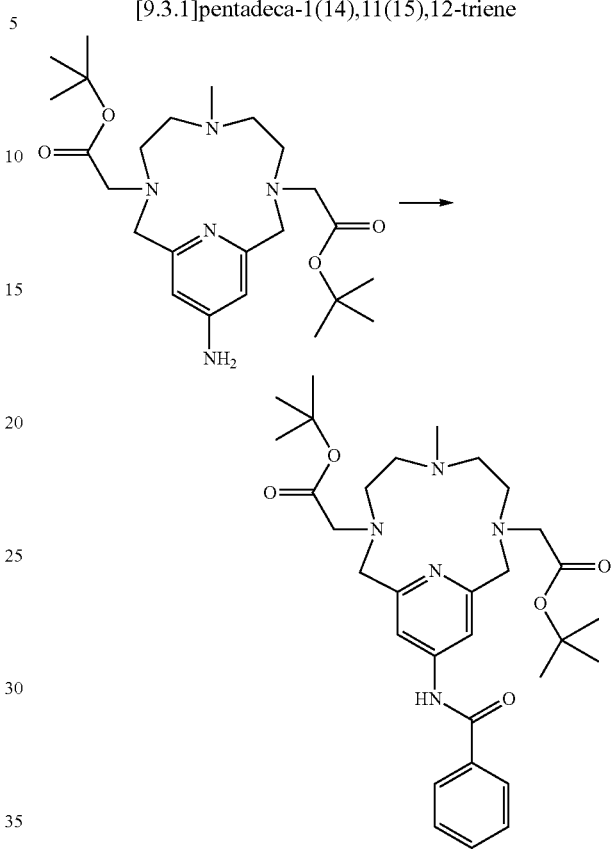

The compound obtained in example 2e (160 mg, 0.35 mmol) is dissolved in acetonitrile (10 mL) and cooled to 0° C. Then benzoyl chloride (93 μL, 0.80 mmol) and potassium carbonate (48 mg, 0.35 mmol) is added and the reaction is allowed to reach room temperature. After 24 h the reaction mixture is concentrated to give crude product. That is used in the next step without purification.

b) Synthesis of manganese complex of N,13-Benzamide-3,6,9,15-tetraaza-3,9-bis-(carboxymethyl)-6-methyl-bicyclo[9.3.1]pentadeca-1(14),11(15),12-triene

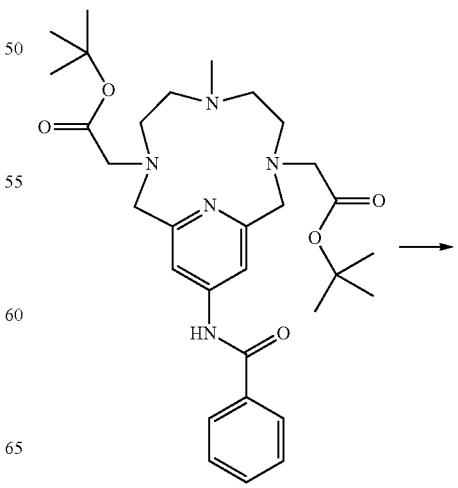

-continued

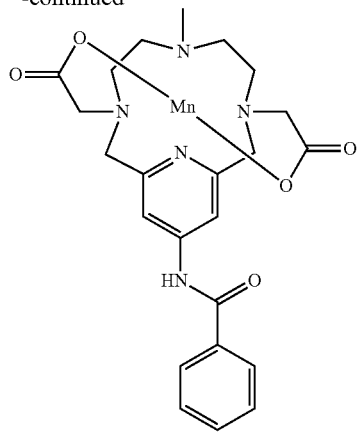

The crude compound obtained in example 6a was dissolved in formic acid and the reaction mixture was refluxed for 1.5 h and then the solvent was evaporated. The crude solid was dissolved in water (10 mL) and the pH was adjusted to 7.1 using NaOH (1M). Then MnCl$_2$ (69 mg, 0.35 mmol) was added and the pH was adjusted to 7 using NaOH (1M). After 2 h the reaction mixture was concentrated and purified by preparative HPLC to give the manganese complex of N,13-Benzamide-3,6,9,15-tetraaza-3,9-bis-(carboxymethyl)-6-methyl-bicyclo[9.3.1]pentadeca-1(14),11(15),12-triene (60 mg, 33%).

What is claimed is:

1. A compound having formula (II)

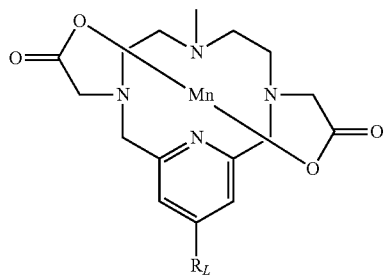

(II)

wherein R$_L$ is a hydrogen or a linker whereby the compound of formula (II) can be linked to another molecule, wherein the linker R$_L$ is selected from group consisting of:

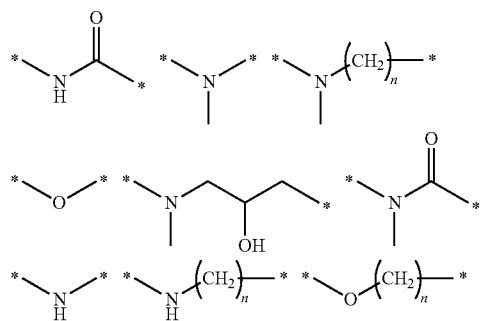

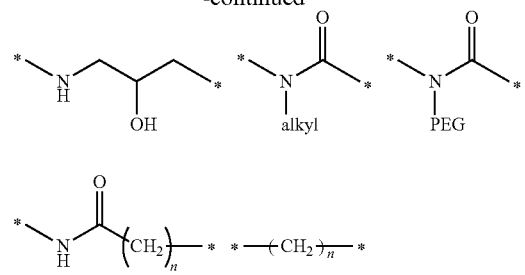

and wherein n is an integer from 1 to 7 and * denotes the position whereby the linker, if present, is attached to the compound and said another molecule.

2. The compound of claim 1, wherein said another molecule is an aromatic ring, inositol or carbohydrate, or any derivative thereof.

3. The compound of claim 1, wherein said another molecule is a natural or synthetic peptide, an amino acid or derivatives thereof, polyamines and derivatives thereof, a peptidomimetic, a polypeptide, a protein, an antibody, a natural or synthetic polymer, a dendrimer, a nanoparticle or a lipophilic compound.

4. The compound of claim 3, wherein said another molecule is a dendrimer.

5. The compound of claim 1, wherein the compound is of the following structures:

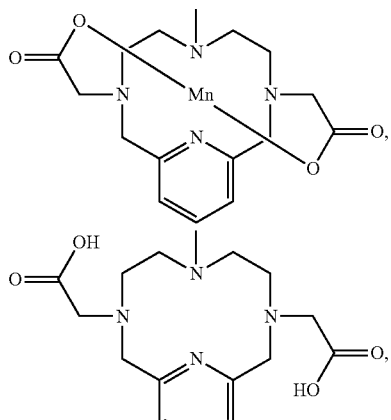

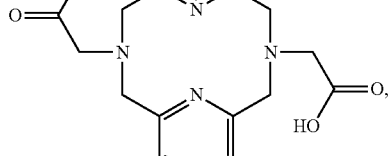

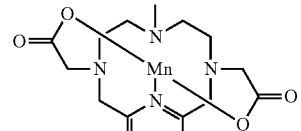

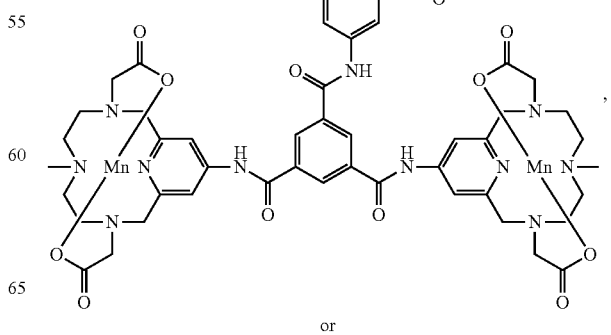

or

-continued

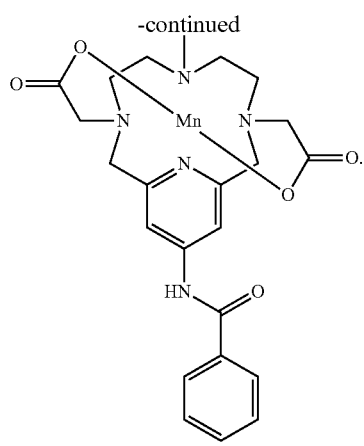

6. A compound having the formula:

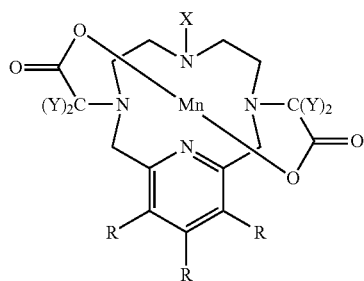

wherein X is alkyl or a linker;
Y is alkyl, —PEG, —COOH, —PO(OH)$_2$, —H, or a linker;
R is alkyl, —PEG, —N(alkyl)$_2$, —N(PEG)$_2$, —O(alkyl), —O(PEG), —NMe$_2$, —NH$_2$, —OMe, —OH, —H, or a linker;
wherein the compound is attached to another molecule if a linker is present;
wherein the linker moiety is selected from group consisting of:

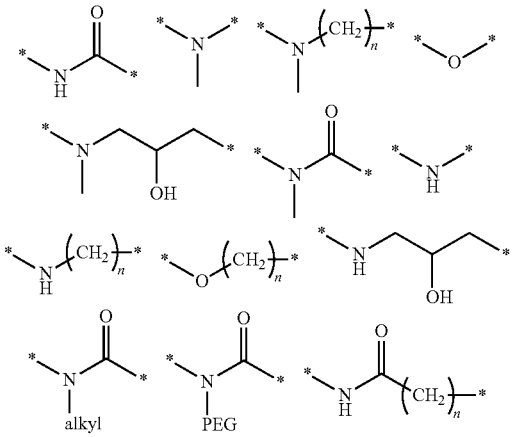

and wherein n is an integer from 1 to 7 and * denotes the position whereby the linker, if present, is attached to the compound and said another molecule.

7. Compound according to claim 6, wherein Y is methyl, —COOH, —PO(OH)$_2$, —H or a linker.

8. Compound according to claim 6, wherein Y is —H or a linker.

9. Compound according to claim 6, wherein R is H, methyl, —NMe$_2$, —NH$_2$, —OMe, —OH or a linker.

10. Compound according to claim 6, wherein the compound is attached to another molecule via said linker.

11. Compound according to claim 10, wherein said another molecule is an aromatic ring, inositol or carbohydrate, or any derivative thereof.

12. Compound according to claim 10, wherein said another molecule is a natural or synthetic peptide, an amino acid or derivatives thereof, polyamines and derivatives thereof, a peptidomimetic, a polypeptide, a protein, an antibody, a natural or synthetic polymer, a dendrimer, a nanoparticle or a lipophilic compound.

13. Compound according to claim 12, wherein said another molecule is a dendrimer.

14. Compound according to claim 6 for use as MR contrast agents.

15. Composition comprising a compound according to claim 6 and at least one physiologically tolerable carrier.

16. Composition according to claim 15 for use as MR contrast medium in MRI.

17. Method of MR imaging wherein a composition according to claim 15 is administered to a subject and the subject is subjected to an MR examination wherein MR signals are detected from the subject or parts of the subject into which the composition distributes and optionally MR images and/or MR spectra are generated from the detected signals.

18. Compound according to claim 6, wherein X is C$_1$-C$_6$ alkyl.

19. A compound of claim 6, having one of the following structures:

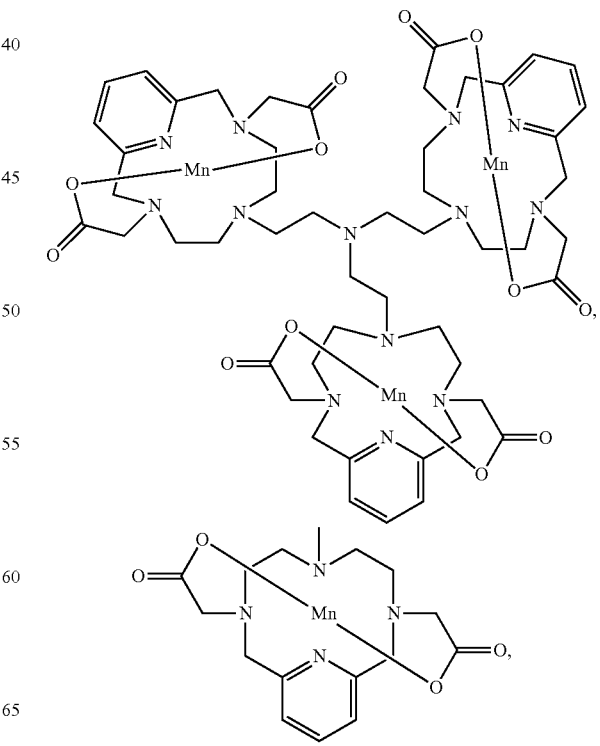

33
-continued
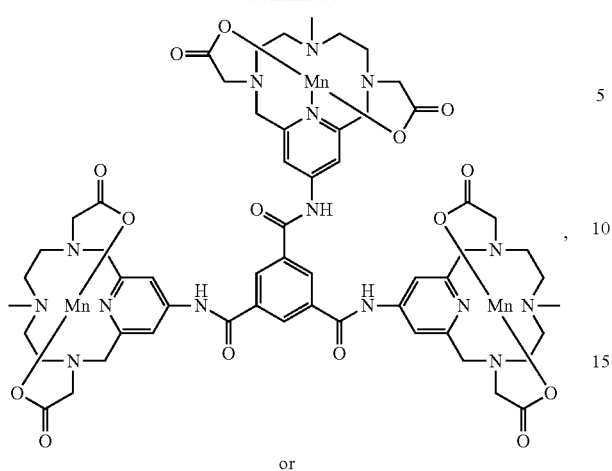
, or
34
-continued
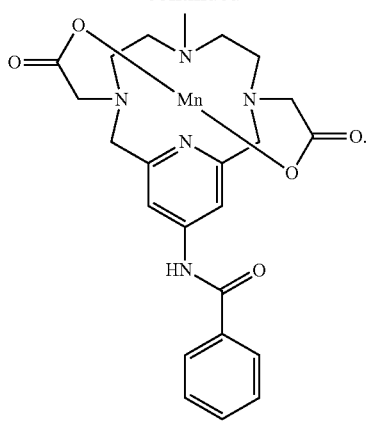
* * * * *